United States Patent
Lothe et al.

(10) Patent No.: US 10,598,663 B2
(45) Date of Patent: Mar. 24, 2020

(54) METHODS AND BIOMARKERS FOR ANALYSIS OF COLORECTAL CANCER

(71) Applicant: Oslo Universitetssykehus HF, Oslo (NO)

(72) Inventors: Ragnhild A. Lothe, Oslo (NO); Jarle Bruun, Oslo (NO); Matthias Kolberg, Oslo (NO); Rolf Inge Skotheim, Oslo (NO); Guro Elisabeth Lind, Oslo (NO); Arild Nesbakken, Røyken (NO)

(73) Assignee: Oslo Universitetssykehus HF, Oslo (NO)

( * ) Notice: Subject to any disclaimer, the term of this patent is extended or adjusted under 35 U.S.C. 154(b) by 82 days.

(21) Appl. No.: 15/302,728

(22) PCT Filed: Apr. 10, 2015

(86) PCT No.: PCT/IB2015/001790
§ 371 (c)(1),
(2) Date: Oct. 7, 2016

(87) PCT Pub. No.: WO2015/193738
PCT Pub. Date: Dec. 23, 2015

(65) Prior Publication Data
US 2017/0038386 A1   Feb. 9, 2017

Related U.S. Application Data

(60) Provisional application No. 61/978,383, filed on Apr. 11, 2014.

(51) Int. Cl.
*G01N 33/574* (2006.01)
*C12Q 1/6886* (2018.01)

(52) U.S. Cl.
CPC ..... *G01N 33/57419* (2013.01); *C12Q 1/6886* (2013.01); *C12Q 2600/118* (2013.01); *C12Q 2600/158* (2013.01); *G01N 2800/52* (2013.01); *G01N 2800/54* (2013.01)

(58) Field of Classification Search
None
See application file for complete search history.

(56) References Cited

U.S. PATENT DOCUMENTS

2013/0130354 A1   5/2013   Gidekel et al.
2015/0141273 A1*  5/2015   Bosch .............. G01N 33/57419
                                                  506/9

FOREIGN PATENT DOCUMENTS

WO   2013/104990   7/2013

OTHER PUBLICATIONS

Mitsuhiro Matsuo et al. "MiR-29c is downregulated in gastric carcinomas and regulates cell proliferation by targeting RCC2" Molecular Cancer, Biomed Central, vol. 12, No. 1, Feb. 25, 2013, p. 15.
Claus Lindbjerg Andersen et al., "Frequent genomic loss at chr16p13.2 is associated with poor prognosis in colorectal cancer", International Journal of Cancer, vol. 129, No. 8, Oct. 15, 2011, pp. 1848-1858.
International Search Report and Written Opinion, International Patent Application No. PCT/IB2015/001790, dated Apr. 10, 2015.

* cited by examiner

*Primary Examiner* — Mark Halvorson
(74) *Attorney, Agent, or Firm* — Casimir Jones S.C.; J. Mitchell Jones (57) ABSTRACT

The present invention relates to methods and biomarkers (e.g., protein biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics.

7 Claims, 6 Drawing Sheets

METHODS AND BIOMARKERS FOR ANALYSIS OF COLORECTAL CANCER

FIELD OF THE INVENTION

The present invention relates to methods and biomarkers (e.g., protein biomarkers) for detection of colorectal cancer in biological samples (e.g., tissue samples, biopsy samples, stool samples, blood samples, plasma samples, serum samples). In some embodiments, methods and biomarkers of the present invention find use in providing a prognosis to colorectal cancer patients, and in companion diagnostics.

BACKGROUND OF THE INVENTION

Colorectal cancer (CRC) is the third most common type of cancer with a worldwide annual incidence of 1.2 million, and mortality rate of approximately 50%. The only available curative treatment for CRC is complete surgical resection of neoplastic tissue (Van Cutsem et al., Colon cancer: Management of locoregional disease, in Kelsen D P, et al., (ed): Principles and practice of gastrointestinal oncology. Philadelphia, USA, Lippincott Williams & Wilkins, 2008, pp 581). Determination of the extent of the disease by clinicopathological tumor staging is the primary prognostic factor for CRC patients (Van Cutstem et al., supra). Despite the favorable outcome for patients with localized stage II tumors compared to stage III tumors, more than 20% of stage II patients suffer from recurrence (Gray et al., Lancet 370: 2020-2029, 2007). Still, investigations of benefit from adjuvant chemotherapy for stage II patients show conflicting results (Andre et al., Ann Surg Oncol 13:887-898, 2006; Sobrero A, Lancet Oncol 7:515-516, 2006; Kohne, Lancet Oncol 7:516-517, 2006), and surgery remains the only recommended treatment modality (Benson et al., J Clin Oncol 22:3408-3419, 2004). For patients with stage III disease, large clinical trials have consistently showed improved survival with administration of adjuvant chemotherapy, and this constitutes the standard of care for this group of patients (Andre et al., N Engl J Med 350:2343-2351, 2004). However, the significantly poorer survival among patients with stage IIB (T-stage 4, lymph node negative) compared to stage IIIA (T-stage 1-2, lymph node positive) disease, underlines the need for refinements to this prognostic stratification (O'Connell et al., J Natl Cancer Inst 96:1420-1425, 2004).

Accordingly, identification of individual patients in need of adjuvant treatment, primarily by predicting prognosis for stage II and III patients remains a major clinical concern. There are currently no markers in routine clinical use for this purpose (Locker et al., ASCO 2006 J Oncol Pract 24:5313-5327, 2006). Hence, identification of molecular markers for prognostic stratification represents a valuable step towards beneficial personalized management of patients with stage II and III disease.

SUMMARY OF THE INVENTION

The present invention relates to methods and biomarkers (e.g., protein biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics. Embodiments of the present invention provide a method for determining a prognosis of colorectal cancer in a subject, predicting the likelihood of recurrence of colorectal cancer in a subject, or selecting a subject with a disease for treatment with a particular therapy, comprising: a) contacting a biological sample from a subject diagnosed with colorectal cancer with a reagent for detecting the level of expression of a regulator of chromosome condensation 2 (RCC2) gene; and b) detecting the level of expression of RCC2 using an in vitro assay, wherein an altered level of expression of RCC2 provides: a prognosis of colorectal cancer in a subject, predicting the likelihood of recurrence of colorectal cancer in a subject, or selecting a subject with a disease for treatment with a particular therapy. In some embodiments, expression or levels of an RCC2 polypeptide is detected. In some embodiments, RCC2 (e.g., RCC2 polypeptide) in the cytosol is detected. In some embodiments, the colorectal cancer informative reagent is for example, an antigen binding protein specific for RCC2 (e.g., an antibody that specifically binds to RCC2). In some embodiments, the biological sample is, for example, a tissue sample, a biopsy sample, a blood sample or a stool sample. In some embodiments, the subject has been previously diagnosed with colorectal cancer. In some embodiments, the subject is a female. In some embodiments, the sample is microsatellite stable (MSS). In some embodiments, a decreased level of expression of RCC2 relative to a reference level of expression of RCC2 is associated with a poor prognosis of the subject. In some embodiments, an increased level of expression of RCC2 relative a reference level of expression of RCC2 is associated with a good prognosis of the subject. In some embodiments, the poor prognosis is, for example, decreased survival, 5 year relapse free survival, or recurrence or metastasis of said colorectal cancer. In some embodiments, the reference level is a level from a subject diagnosed with colorectal cancer or a subject not diagnosed with colorectal cancer. In some embodiments, the method further comprises the step of determining a treatment course of action. In some embodiments, the treatment course of action comprises administering chemotherapy to subjects identified as having a poor prognosis and not administering chemotherapy to subjects identified as having a good prognosis. In some embodiments, the chemotherapy is adjuvant chemotherapy. In some embodiments, the colon cancer is stage I, II, III or IV.

Further embodiments provide a kit, comprising: one or more colorectal informative reagents for detecting altered gene expression in a sample from a subject having or suspected of having colorectal cancer of RCC2.

Additional embodiments provide the use of the kit for diagnosing colorectal cancer in a subject or determining the likelihood of success of a specific treatment and/or selecting patient for the treatment.

Yet other embodiments provide a reaction mixture, comprising a colorectal cancer informative reagent complexed to a RCC2 polypeptide.

Some embodiments provide a method for detecting the presence of a regulator of chromosome condensation 2 (RCC2) gene, comprising: a) contacting a microsatellite stable (MSS) biological sample from a female subject diagnosed with colorectal cancer with a reagent for detecting the level of expression of a regulator of chromosome condensation 2 (RCC2) gene; and b) detecting the level of expression of the RCC2 using the reagent.

Additional embodiments will be apparent to persons skilled in the relevant art based on the teachings contained herein.

DESCRIPTION OF THE DRAWINGS

FIG. 1 shows a flow diagram for inclusion of patients in the study. Tissue from four patients with endoscopic procedure included. From patients with synchronous tumors only one tumor was randomly selected for mutation analyses. Un-evaluable tissue had insufficient number of epithelial tumor cells, extensive necrosis and/or poor tumor preservation.

DEFINITIONS

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the terms "colorectal cancer informative reagent" refers to a reagent or reagents that are informative for identification of expression of cancer gene markers described herein. In some embodiments, reagents are primers, probes or antibodies for detection of gene expression products (e.g., RNA transcripts or proteins) of RCC2.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized colorectal cancer cells" is meant to refer to colorectal cancer cells which have metastasized; colorectal cancer cells localized in a part of the body other than the colorectal.

As used herein, "an individual is suspected of being susceptible to metastasized colorectal cancer" is meant to refer to an individual who is at an above-average risk of developing metastasized colorectal cancer. Examples of individuals at a particular risk of developing colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "colorectal neoplasm-specific marker" refers to any biological material that can be used to indicate the presence of a colorectal neoplasm (e.g., a premalignant colorectal neoplasm, a malignant colorectal neoplasm, a metastatic colorectal neoplasm). Examples of colorectal neoplasm-specific markers include, but are not limited to, the 13 gene signature described herein.

A "sequence" of a biopolymer refers to the order and identity of monomer units (e.g., amino acids, etc.) in the biopolymer.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "locus" as used herein refers to a nucleic acid sequence on a chromosome or on a linkage map and includes the coding sequence as well as 5' and 3' sequences involved in regulation of the gene.

DETAILED DESCRIPTION OF THE INVENTION

The present invention relates to methods and biomarkers (e.g., protein biomarkers) for detection of colorectal cancer in biological samples (e.g., tissue samples, biopsy samples, stool samples, blood samples, plasma samples, serum samples). In some embodiments, methods and biomarkers of the present invention find use in providing a prognosis to colorectal cancer patients, and in companion diagnostics.

With few exceptions, clinicopathological factors are used to predict prognosis and they do not have a high level of precision. Perforation of the tumour during surgery and too few examined lymph nodes are associated with reduced survival for stage II CRC, and are usually considered indications for adjuvant chemotherapy. A proportion of stage II patients without increased risk of relapse based on clinical factors still develop relapse. A significant proportion of stage III patients would survive without chemotherapy. Finally, in the metastatic setting prognostic factors are highly warranted to provide prognoses and guide treatment decisions.

Only one prognostic molecular marker is recommended for clinical use: microsatellite instability (MSI), which accounts for about 12-15% of all cases. Among the remaining cases (85%), the RCC2 marker has strong implications for female patients, >40% of all CRC. Furthermore, among the large gender specific group of microsatellite stable (MSS) tumors RCC2 identifies high risk patients among the stage I-II, which is assumed to be cured by surgery alone and among rectal cancer patients. Given the high incidence of CRC, the compositions and methods described herein are beneficial for a large number of patients.

Adjuvant chemotherapy significantly improves survival in stage III CRC and is accepted as standard treatment of these patients. The majority of stage II CRC patients are cured by surgery alone, but there are indications that the proportion of stage II patients who still develop relapse would benefit from adjuvant chemotherapy. This highlights the need for biomarkers for more precise prediction of high risk stage II patients, and consequently also improved individualized cancer care. On the other hand, there are patients in stage III that will be cured by surgery alone and do not need adjuvant chemotherapy. If they were pinpointed at time of diagnosis, severe side effects are avoided, improving quality of life for the patient. Furthermore, there are elderly state III patient who currently do not receive adjuvant chemotherapy, and who may benefit from such treatment.

Accordingly, embodiments of the present disclosure provide a solution to the unmet need for a prognostic marker for use in providing prognoses and determining treatment courses of action in CRC patients. In experiments conducted during the course of development of embodiments of the present disclosure, weak cytosolic staining of RCC2 was significantly associated with overall poor prognosis ($p=5\times10^{-7}$) and with time to recurrence ($p=8\times10^{-5}$), the latter including only patients (n=619) with complete resection (R0). Cox proportional hazards regression modelling including known clinical factors showed interaction between RCC2 staining (both cytosolic and nuclear) and gender for the survival analyses. Subsequent sub-group analyses showed significant association between low RCC2 expression and poor survival among female patients (cytosolic: $p=6\times10^{-6}$ and nuclear: $p=0.001$).

Further stratification showed significant association between low RCC2 and poor prognosis confined to female patients with microsatellite stable tumors (often referred to as chromosomal unstable), accounting for about 40% of all primary CRC. Additional clinically relevant subgroup associations were found for low RCC2 and poor prognosis among stage I and II, and among rectal cancers.

I. Diagnostic and Screening Methods

As described above, embodiments of the present invention provide diagnostic, prognostic, research, and screening methods that utilize the detection of altered levels of protein expression of cancer marker genes (e.g., RCC2). In some embodiments, the methods and kits utilize colorectal cancer informative reagents for the detection of a gene product (e.g., RCC2 polypeptide). In some embodiments, compositions and methods for detecting the presence of RCC2 gene in a microsatellite stable (MSS) biological sample from a female subject diagnosed with colorectal cancer (e.g., for research or screening uses) are provided.

Any patient sample suspected of containing the genes may be tested according to methods of embodiments of the present invention. By way of non-limiting examples, the sample may be tissue (e.g., a colorectal biopsy sample or other tissue sample), blood, stool or a fraction thereof (e.g., plasma, serum, etc.).

While the present invention exemplifies RCC2 for detecting and providing a prognosis for colorectal cancer, any marker that is correlated with the presence or absence of colorectal cancer may be used, alone or in combination with the markers described herein. A marker, as used herein, includes, for example, nucleic acid(s) whose production or mutation or lack of production is characteristic of a colorectal neoplasm or a prognosis thereof. Depending on the particular set of markers employed in a given analysis, the statistical analysis will vary. For example, where a particular combination of markers is highly specific for colorectal cancer, the statistical significance of a positive result will be high. It may be, however, that such specificity is achieved at the cost of sensitivity (e.g., a negative result may occur even in the presence of colorectal cancer). By the same token, a different combination may be very sensitive (e.g., few false negatives, but has a lower specificity).

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action. Markers for other cancers, diseases, infections, and metabolic conditions are also contemplated for inclusion in a multiplex or panel format.

The methods are not limited to a particular type of mammal. In some embodiments, the mammal is a human. In some embodiments, the colorectal neoplasm is premalignant. In some embodiments, the colorectal neoplasm is malignant. In some embodiments, the colorectal neoplasm is colorectal cancer without regard to stage of the cancer (e.g., stage I, II, III, or IV). In some embodiments, the colorectal cancer is stage II.

RCC2 polypeptides described herein may be detected as proteins using a variety of techniques known to those of ordinary skill in the art, including but not limited to: immunoassays.

Illustrative non-limiting examples of immunoassays include, but are not limited to: immunoprecipitation; Western blot; ELISA; immunohistochemistry; immunocytochemistry;

flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

II. Data Analysis

In some embodiments, a computer-based analysis program is used to translate the raw data generated by the detection assay (e.g., the expression level a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or stool sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a stool sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., prognosis of disease free survival or metastasis) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

III. Compositions & Kits

Compositions for use in the diagnostic methods described herein include, but are not limited to, kits comprising one or more colorectal cancer informative reagents as described above. In some embodiments, the kits comprise one or more colorectal cancer informative reagents for detecting altered RCC2 protein expression in a sample from a subject having colorectal cancer.

In some embodiments, the kits contain colorectal cancer informative reagents specific for a cancer gene marker, in addition to detection reagents and buffers.

In preferred embodiments, the colorectal informative reagent is an antigen binding protein(s) that binds to a respective gene product(s) of the one or more genes. The antibody compositions of the present invention may also be provided in the form of an array. In preferred embodiments, the kits contain all of the components necessary to perform a detection assay, including all controls, directions for performing assays, and any necessary software for analysis and presentation of results.

In some embodiments, the present disclosure provides reaction mixtures comprising a complex of a colorectal cancer specific detection reagent that specifically detects (e.g., binds) RCC2 and an RCC2 polypeptide.

III. Methods of Use

As disclosed herein, the present invention provides colorectal cancer informative reagents and methods for determining a prognosis of colorectal cancer in a subject, predicting the likelihood of recurrence of colorectal cancer in a subject, or selecting a subject with a disease for treatment with a particular therapy. The colorectal cancer can be stage I, II, III, or IV colorectal cancer. In some preferred embodiments, embodiments of the present invention provide compositions and methods for providing a prognosis to a patient diagnosed with colorectal cancer (e.g., stage II colorectal cancer). For example, in some embodiments, altered expression relative to a control sample (e.g., non-cancerous colorectal tissue or stage I or IV colorectal cancer) of RCC2 relative to a reference level of expression in a control sample of the genes is associated with a poor prognosis (e.g., decreased survival or increased risk of metastasis). In some embodiments, the reference level is from a subject diagnosed with stage I or IV colorectal cancer. In some embodiments, the reference level is from a subject not diagnosed with colorectal cancer. In some embodiments, the level of expression as compared to the reference level is indicative of a poor prognosis. In some embodiments, the poor prognosis is a decreased chance of survival. In some embodiments, the poor prognosis is an increased chance of recurrence or metastasis of colorectal cancer. In some embodiments, the prognosis is the likelihood of 5 year relapse free survival.

In some embodiments, the prognostic information is used to determine a treatment course of action for the subject. For example, in some embodiments, subjects found to have a poor prognosis can be given adjuvant chemotherapy, while subjects with a good prognosis can be treated with surgery alone. In further embodiments, the assays of the present invention are utilized during clinical testing of therapeutic agents for colorectal cancer. It is contemplated that the assays for gene products as described above will define specific patient populations for which treatment with the therapeutic agent is more or less effective than the patient population as a whole. Thus, in some embodiments of the present invention, methods are provided where subjects are screened using the assays of the present invention and patients with a particular profile of gene expression as described above are selected for treatment with a particular therapeutic agent or therapeutic regime.

EXPERIMENTAL

The following examples are provided in order to demonstrate and further illustrate certain preferred embodiments and aspects of the present invention and are not to be construed as limiting the scope thereof.

Example 1

Materials and Methods

Patient Samples

Figure 1:
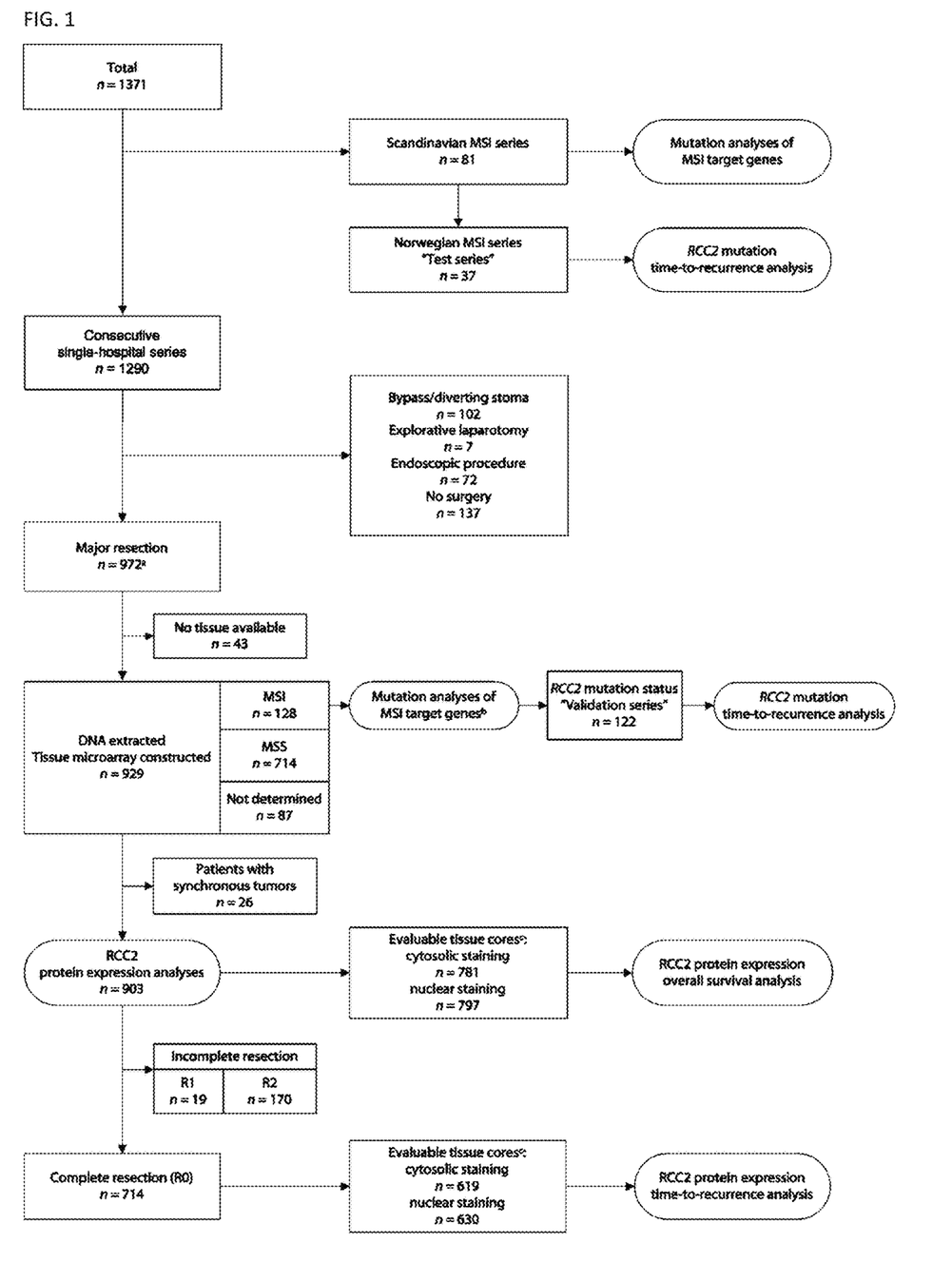
Figure 2:
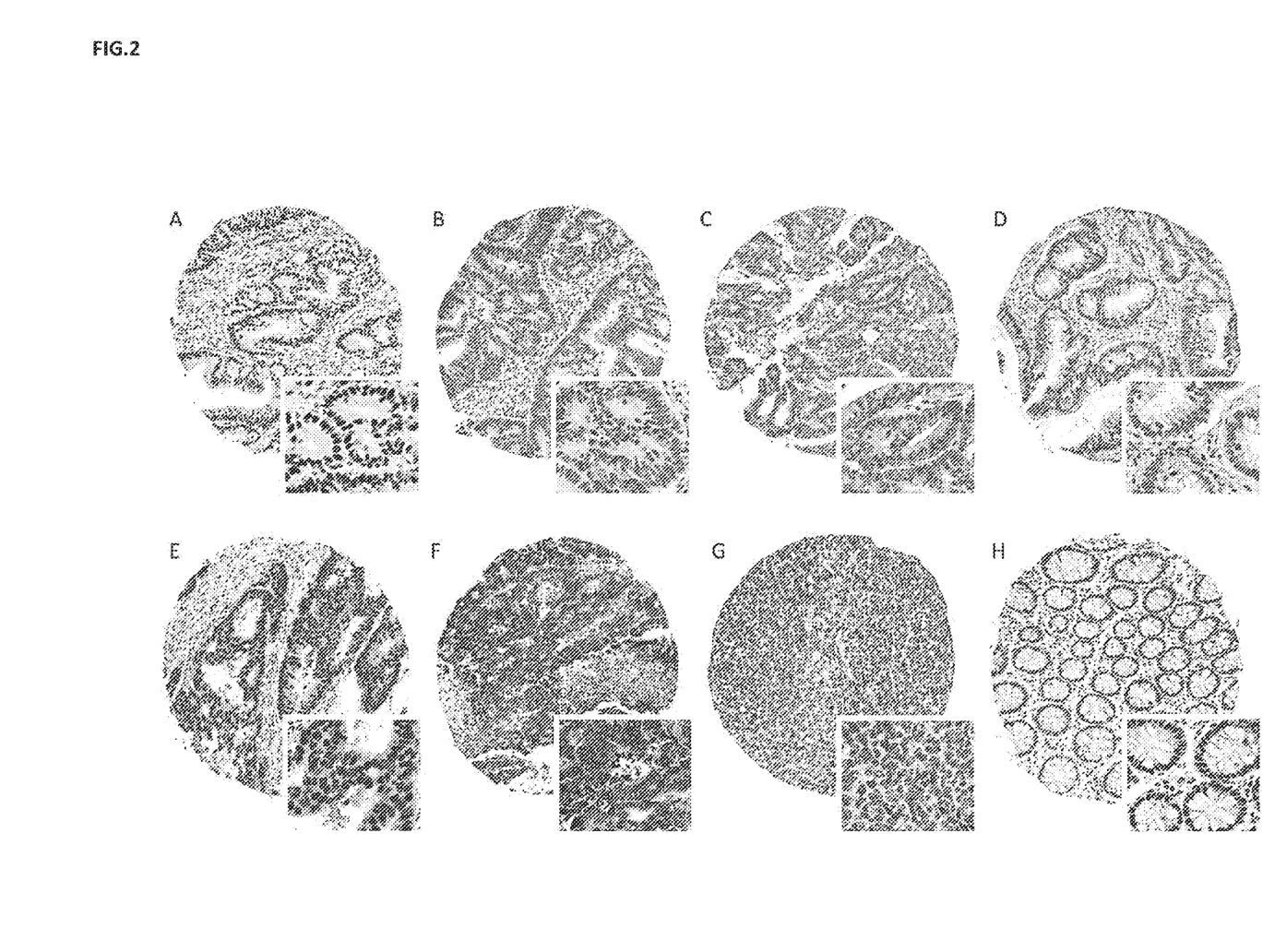
FIG. 2 shows differential immunohistochemical staining of RCC2 in colorectal carcinomas. Representative staining of histospots (core diameter 0.6 mm) is illustrated at 400× magnification. (A-D) Strong-, moderate-, weak- and negative nuclear staining, respectively. (E) Strong nuclear and cytosolic staining (F) Predominant cytosolic staining. (G) Staining in undifferentiated tissue. (H) Staining in normal colon.

A population-representative consecutive series of 1290 CRC patients admitted to Oslo University Hospital—Aker (1993-2003) was analyzed. Of these, 929 patients underwent major resection where DNA was extracted and a tissue microarray was constructed (FIG. 1). Major resection was defined as removal of the tumor-bearing bowel segment with the lymphovascular pedicle and mesentery. TNM-staging and histopathological grading followed the UICC/AJCC system, version 5. Relevant clinical data had been prospectively registered. All samples were formalin-fixed and embedded in paraffin. MSI status was previously determined for most tumors (Merok et al, *Ann. Oncol.* 2012). Additionally, a set of samples (n=16) with no determined MSI status was reanalyzed in order to extend the MSI series, yielding a total of 128 MSI positive tumors (122 with RCC2 mutation status), constituting the Norwegian series for mutation analyses and the validation series for prognostic analyses.

Determination of MSI

MSI status was determined using the consensus markers provided by the National Cancer Institute (BAT25, BAT26, D2S123, D5S346 and D17S250) (Boland et al, *Cancer Res.* 58: 5248-5257 1998). The PCR protocol was optimized both for DNA from fresh frozen tissue and for DNA from formalin-fixed samples as described in (Diep et al, *J. Clin. Oncol.* 21: 820-829 2003; Merok et al, *Ann. Oncol.* 2012). Samples that showed instability for two or more of the markers were classified as MSI-H, the ones with only one unstable marker were classified as MSI-L, while samples with no unstable markers were classified as MSS. Tumors with MSI-H are here referred to as MSI, while tumors with MSI-L and MSS are grouped and denoted MSS.

Primary Antibodies

For immunohistochemistry, rabbit polyclonal anti-RCC2 antibodies were obtained from Novus Biologicals (Cat. No. NB110-40619, Cambridge, UK), recognizing a C-terminal epitope between residue 471 and residue 522, and employed at a 1:500 dilution.

In Situ Protein Expression Analysis

Formalin-fixed and paraffin-embedded tissue from 670 colonic, 233 rectal and 26 synchronous carcinomas from patients treated at Oslo University Hospital—Aker (1993-2003), was organized into a tissue microarray according to the original method described by Kononen and colleagues in 1998 (Kononen et al, *Nat. Med.* 4: 844-847 1998). The in situ protein expression analysis was done on 3 μm thick sections on microscope slides, and was performed as previously described (Skotheim et al, *Neoplasia.* 5: 397-404 2003). In brief, sections were de-paraffinized in xylene for 10 minutes, and then rehydrated. Antigen retrieval was performed in a microwave oven by heating the sections in plastic containers filled with Tris-buffer (pH=9). Staining was performed according to the DAKO Envision protocol, using the reagents supplied with the K5007 kit (Dako, Glostrup, Denmark). A test tissue microarray containing representative tissues from nine human organs and six types of cancer was utilized to optimize staining conditions. A negative control experiment was provided by omitting the primary antibody from one slide. The staining of RCC2 was scored according to the proportion and intensity categories proposed by Allred et al. (Allred et al, *Mod. Pathol.* 11: 155-168 1998). The proportion score represents the estimated fraction of positive cells (0=none, 1=less than 1%, 2=1-10%, 3=11-33%, 4=34-66% and 5=67-100%), while the intensity score represents their average staining intensity (0=negative, 1=weak, 2=intermediate, 3=strong). Expression was scored separately for cytoplasmic and nuclear staining patterns. Tumors with a score above 4 were termed strong, while tumors with score 4 and below were termed weak. The scoring was performed independently by two investigators, blinded to clinical data, in close collaboration with an experienced pathologist. The interobserver agreement was strong with intraclass correlation coefficients (ICC) of 0.89 and 0.67 for nuclear and cytosolic staining, respectively. Calculations were confirmed by cross tabular visualizations. All discrepancies were resolved and reassigned on consensus of opinion.

Statistical Methods

Five-year overall survival and time-to-recurrence plots were generated using the Kaplan-Meier method in the SPSS 18.0 software (SPSS, IL, USA). The logrank test was used to compare survival curves. Multivariate Cox proportional hazards regression modeling was employed to determine parameters with significant independent impact on patient survival. The proportional hazards assumptions were verified by graphical evaluation of plots of log(-log survival time) versus log time. Time-to-recurrence and overall survival was defined according to the guidelines given by Punt et al. (Punt et al, *J. Natl. Cancer Inst.* 99: 998-1003 2007). Time-to-recurrence was defined as the time from surgery to the first event of either death from the same cancer, local recurrence or distant metastasis. Patients were censored at death from other cancer, non-cancer death, post-operative death (<3 months) and loss to follow-up. Overall survival was defined as the time from surgery to death from any cause, and patients were censored at loss to follow-up. All P-values were two-sided and derived from statistical tests using SPSS, and considered statistically significant at $P \leq 0.05$. A senior statistician was consulted to ensure proper use of statistical methodology.

Results

The in situ protein expression of RCC2 was investigated in a consecutive single-hospital series of primary colorectal cancers (n=903, FIG. 1), including the two main subgroups of CRC, MSI (n=122, MSI validation series) and MSS (n=714) tumors.

Staining of tumor sections using an RCC2 selective antibody demonstrated a specific staining in both the cytosol and in the nuclei of the cells (FIG. 2A-H). The staining was largely confined to epithelial cells, but some scattered staining was also observed in the tumor stroma.

Figure 3:
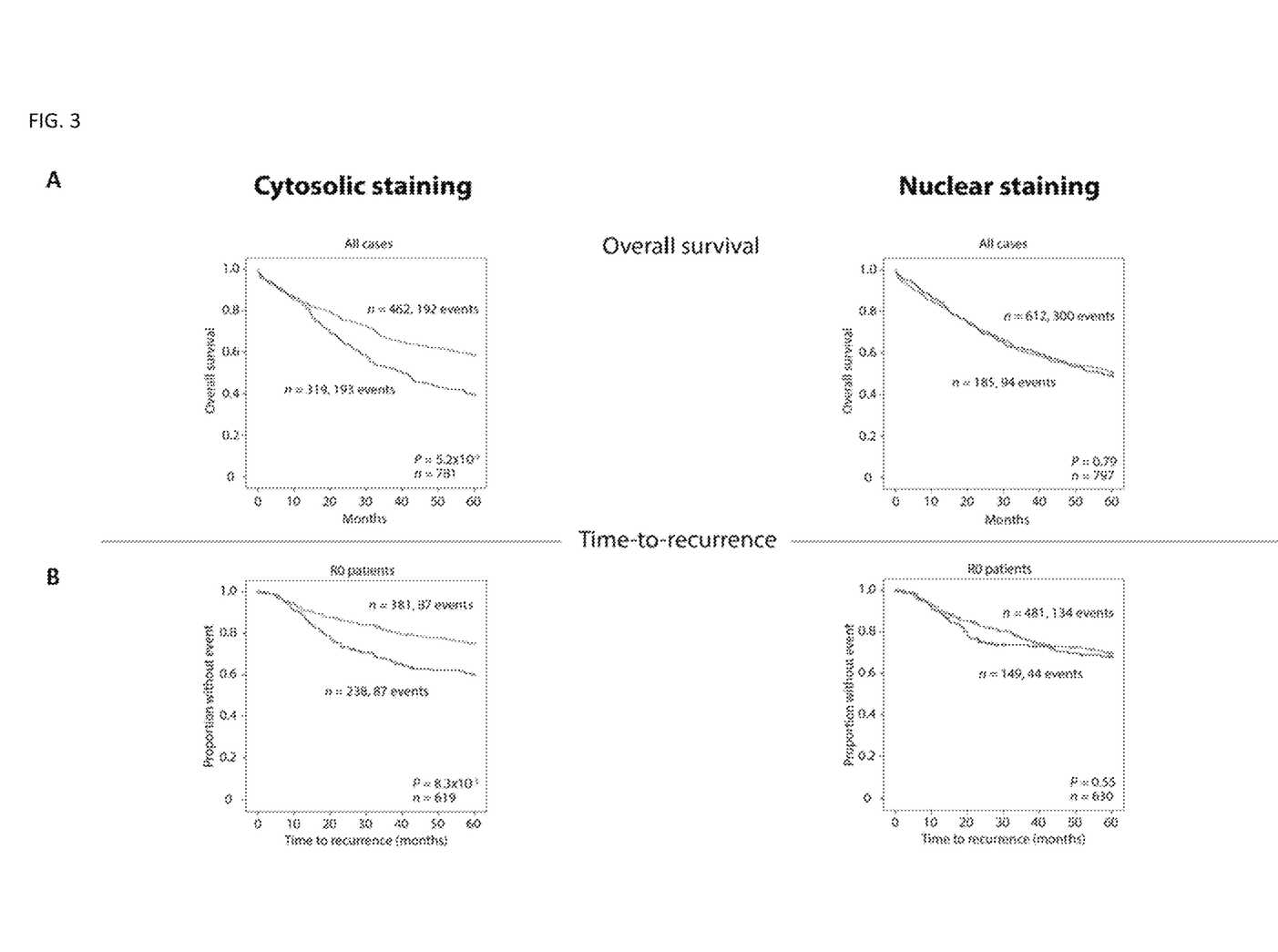
FIG. 3 shows survival analysis for RCC2 cytosolic (left) and nuclear (right) protein expression in a consecutive CRC series (n=903). (A) Five-year overall survival. (B-D) Five-year time-to-recurrence analysis for patients with complete resection (R0, no evidence of residual tumor). (C) Subgroup analysis for gender. (D) Subgroup analysis for gender and MSS. The Kaplan-Meier method (logrank test) was used to draw the plots and determine statistical differences between patients with strong and weak RCC2 staining.

In situ protein expression of RCC2 for the consecutive CRC series was evaluated on the tissue microarray (n=903) with 781 and 797 evaluable tissue cores for cytosolic and nuclear staining, respectively. Overall survival and time-to-recurrence Kaplan-Meier analyses were performed to test for an association between RCC2 staining and survival. For cytosolic staining, both overall survival (FIG. 3A) and time-to-recurrence (FIG. 3B) analyses showed significant associations with patient outcome ($P=5.2 \times 10^{-7}$, n=781 and $P=8.3 \times 10^5$, n=619). The time-to-recurrence analysis was restricted to R0 patients. For overall survival, patients with strong cytosolic expression had a five-year overall survival of 58%, while patients with weak cytosolic expression had a five-year overall survival of 39%. Cox proportional hazards regression modeling including relevant background and clinical variables showed significant interaction between RCC2 cytosolic staining and gender, both for overall survival (Table 1) ($P=0.0059$ for the interaction test and $P=0.0015$ for RCC2) and for time-to-recurrence analysis (Table 2) ($P=0.0037$ for the interaction test and $P=1.4 \times 10^{-5}$ for RCC2). Subsequent subgroup analysis (time-to-recurrence) for gender (FIG. 3C) revealed significant associations confined to female patients ($P=6.2 \times 10^{-6}$, n=316, for females, and $P=0.27$, n=303, for males). Further stratification on female MSS/MSI status showed that this was confined to patients with MSS (FIG. 3D). There was a significant relationship between MSS/MSI-status and RCC2 cytosolic staining ($P=0.012$, Fisher's exact test, n=712), indicating an association.

After five years follow-up, only 21% of female MSS-patients with R0 status and strong RCC2 cytosolic staining in their tumor tissue had experienced relapse in contrast to 53% of patients with weak RCC2 cytosolic staining ($P=3.9 \times 10^{-7}$, n=232). The corresponding five-year overall survival was 36% and 74% ($P=6.5 \times 10^{-8}$, n=232).

Importantly, Spearman's p test (exact) revealed a significant correlation between RCC2 cytosolic staining and tumor stage ($P=2.1 \times 10^{-4}$, n=777). Weak cytosolic staining was more predominant among stage III and IV tumors than among stage I and II tumors.

Figure 4:
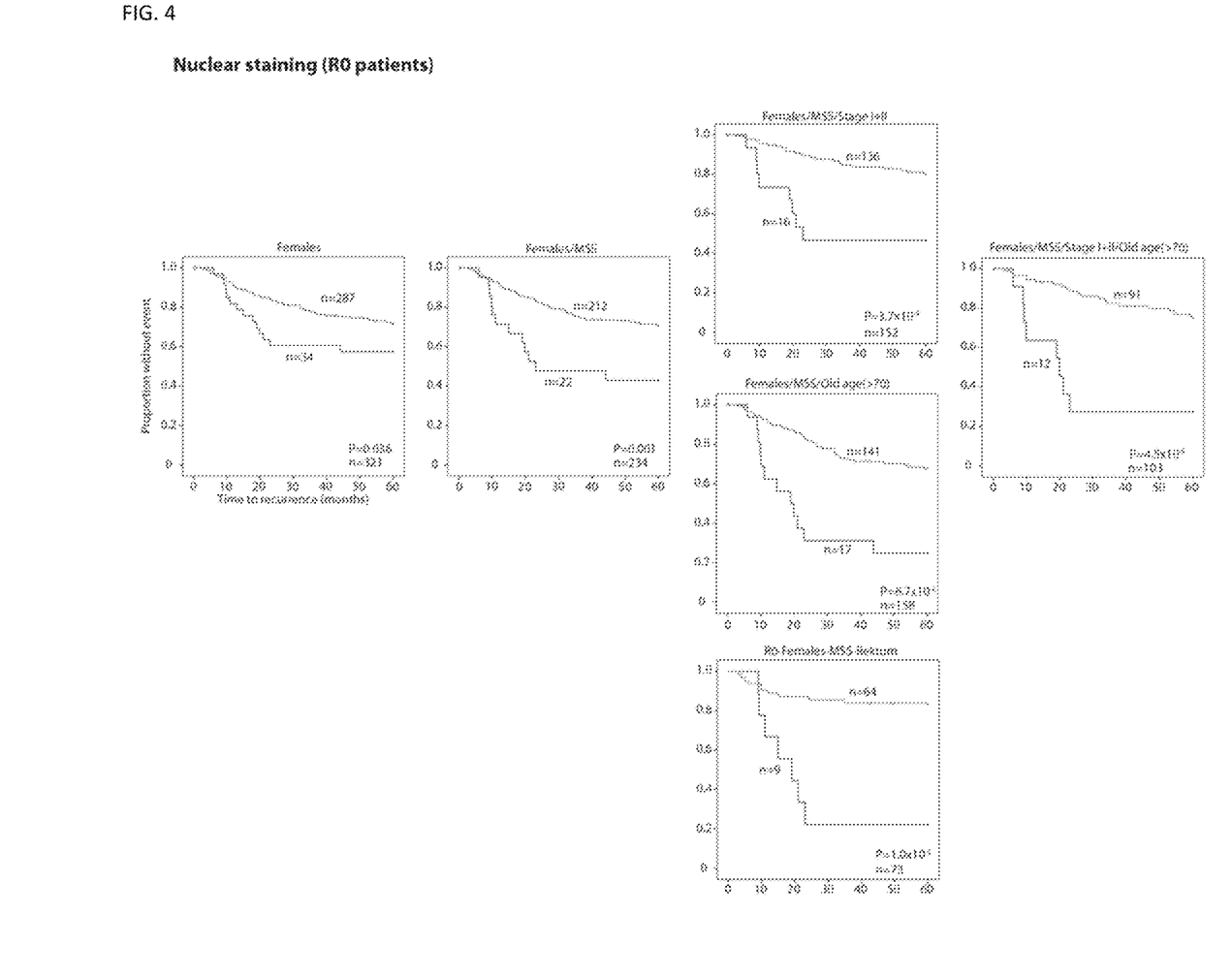
FIG. 4 shows subgroup analysis of in situ expression of RCC2 for a consecutive CRC series. Kaplan-Meier survival analysis for RCC2 nuclear (upper) and cytosolic (lower) staining.

Nuclear expression of RCC2 had no impact on five-year overall survival ($P=0.79$, n=797) (FIG. 3A) or five-year time to recurrence ($P=0.55$, n=630) (FIG. 3B). However, multivariate Cox proportional hazards regression modeling (time-to-recurrence, including adjustment for gender, age, MST/MSS-status, and tumor location, differentiation and stage) showed significant interaction with gender ($P=0.016$, HR 3.0, CI 1.2-7.3 for the interaction test and $P=0.001$, HR 2.9, CI 1.6-5.3 for RCC2). Nuclear staining subgrouped by gender showed significant associations for female patients (P=0.045, n=321, for females, and P=0.30, n=309, for males). Further stratification on female MSS/MST-status indicated significant associations confined to female MSS patients (P=0.013, n=234, for MSS, and P=0.93, n=66, for MST). Further explorative subgroup analyses indicated several clinically and functionally relevant associations: to old age (>70 years), rectal cancer and stage I/II disease (FIG. 4).

Spearman's ρ correlation test of in situ RCC2 protein expression for the validation series of MST cancers did not reveal any significant differences in level of cytosolic (P=0.47, n=101) or nuclear (P=0.50, n=98) RCC2 staining between tumors with wild type and mutated MNR in the 5'UTR of RCC2.

The present study connects RCC2 directly to cancer in general and to CRC in particular. In situ protein expression analysis of RCC2 in the consecutive CRC series revealed that patients with weak cytosolic RCC2 staining had a poor prognosis relative to patients with strong cytosolic RCC2 staining. Statistical tests for interaction demonstrated particular relevance for female patients, and subgroup analyses showed striking differences in the MSS group, for both cytosolic and nuclear staining.

A potential explanation for why reduced RCC2 protein expression in MSS tumors is associated with poor prognosis can be drawn from a study identifying RCC2 as a key player in the integrin $\alpha_5\beta_1$-fibronectin signaling network (Humphries et al, 2009). These experiments in MEF and B16-F10 cells showed that RCC2 serves as a negative regulator of RAC1 and ARF6, and showed that RCC2 knockdown resulted in accelerated cell spreading, cell adhesion and reduced directional cell migration. The authors indicated that RCC2 regulates and limits the required signaling by RAC1 and ARF6 to enable proper membrane protrusion and delivery. It is contemplated that strong cytosolic staining for the RCC2 protein in CRC indicates active RAC1 and ARF6 inhibition, and that weak RCC2 staining relates to aberrant regulation of RAC1 and ARF6 leading to an increased migratory and metastatic potential. The latter is in keeping with a significant correlation between cytosolic RCC2 expression and tumor stage, as stage I and II tumors more often have strong cytosolic staining, and stage III and IV tumors more often have weak cytosolic staining. In line with this scenario, a recent study demonstrated that RCC2 forms a complex with the well-established F-actin regulator cortactin (Grigera et al, *J. Proteomics* 2012), providing further support for a connection between RCC2 and cell motility and invasion. Cortactin, together with among others RAC1, is tightly involved in the generation of cell membrane protrusions, such as lamellipodias and invadopodias, and several studies have described the role of cortactin plays in cancer development (Kirkbride et al, *Cell Adh. Migr.* 5: 187-198 2011). As MSS tumors already suffer from a deranged mitotic apparatus, they might not experience severe negative effects following a reduced level of RCC2 protein. Instead, reduced levels of RCC2 protein might primarily lead to deregulation of RAC1, ARF6 and/or cortactin, followed by increased migratory and invasive properties. A model of this network has been proposed (Byron et al, *Sci. Signal.* 4: t2 2011), placing RCC2 between cortactin and RAC1, enabling a dynamic interplay among these partners with probable relevance to cancer development. Together, these data add cancer as an important dimension to the current RCC2 framework, and show that RCC2 serves as a prognostic biomarker for CRC.

TABLE 1

Univariate and multivariate analyses of correlation of cytosolic RCC2 in situ protein expression with overall survival in a consecutive CRC series.

| Variable | Patients n (%) | Univariate analysis[a] 5-year OS/ TTR (%) | P | Multivariate analysis[b] HR | 95% CI | P |
|---|---|---|---|---|---|---|
| Overall survival | | | | | | |
| Total Gender | 903 (100) | | | | | |
| Female | 474 (52) | 49.6 | | 1 | | |
| Male | 429 (48) | 51.0 | 0.40 | 0.83 | 0.61-1.14 | 0.25 |
| Age[c] | | — | | 1.04 | 1.03-1.05 | $3.4 \times 10^{-13}$ |
| RCC2 cytosolic staining | | | | | | |
| Weak | 319 (35) | 39.5 | | 1 | | |
| Strong | 462 (51) | 58.4 | $5.2 \times 10^{-7}$ | 0.61 | 0.45-0.83 | 0.0015 |
| ND* | 122 (14) | | | | | |
| Stage | | | | | | |
| I | 133 (15) | 77.4 | | 1 | | |
| II | 363 (40) | 62.3 | | 1.61 | 1.03-2.52 | |
| III | 237 (26) | 47.3 | | 2.49 | 1.59-3.91 | |
| IV | 165 (18) | 6.7 | $1.6 \times 10^{-56}$ | 3.66 | 2.00-6.70 | $9.5 \times 10^{-6}$ |
| ND* | 5 (1) | | | | | |
| Tumor location | | | | | | |
| Proximal colon | 367 (41) | 48.2 | | 1 | | |
| Distal colon | 302 (33) | 46.4 | | 0.98 | 0.76-1.27 | |
| Rectum | 234 (26) | 58.5 | 0.0061 | 0.86 | 0.63-1.17 | 0.59 |
| Histopathologic grade | | | | | | |
| G1 | 84 (9) | 63.1 | | 1 | | |
| G2 | 674 (75) | 51.0 | | 1.17 | 0.76-1.79 | |
| G3 | 108 (12) | 33.3 | $1.6 \times 10^{-7}$ | 2.64 | 1.60-4.37 | $1.1 \times 10^{-6}$ |

TABLE 1-continued

Univariate and multivariate analyses of correlation of cytosolic RCC2 in situ protein expression with overall survival in a consecutive CRC series.

| | | Univariate analysis[a] | | Multivariate analysis[b] | | |
|---|---|---|---|---|---|---|
| | Patients | 5-year OS/ | | | | |
| Variable | n (%) | TTR (%) | P | HR | 95% CI | P |
| Mucinous* | 12 (1) | | | | | |
| ND* | 25 (3) | | | | | |
| MSI/MSS | | | | | | |
| MSI | 119 (13) | 58.8 | | 1 | | |
| MSS | 700 (78) | 48.1 | 0.039 | 1.99 | 1.33-2.98 | 0.0085 |
| ND* | 84 (9) | | | | | |
| Residual tumor | | | | | | |
| R0 | 714 (79) | 61.2 | | 1 | | |
| R1 | 19 (2) | 42.1 | | 1.73 | 0.81-3.70 | |
| R2 | 170 (19) | 5.9 | $6.2 \times 10^{-85}$ | 3.48 | 2.23-5.42 | $1.3 \times 10^{-7}$ |
| Interaction parameter | | | | | | |
| Gender x RCC2 | | | | 1.84 | 1.19-2.84 | 0.0059 |

[a]Kaplan-Meier estimate (logrank test).
[b]Cox regression model (Wald test) - all included parameters are displayed in the table.
[c]Hazard ratios are given per year of age.
*Excluded from the statistical analyses.
Abbreviations:
G1 - High differentiation;
G2 - Moderate differentiation;
G3 - Poor differentiation;
R0 - Complete resection - no residual tumor;
R1 - microscopic residual cancer at the resection margin;
R2 - Macroscopic or radiological evidence of residual cancer, locally or distant.

TABLE 2

Univariate and multivariate analyses of correlation of cytosolic RCC2 in situ protein expression with time-to-occurrence in a consecutive CRC series.

| | | Univariate analysis[a] | | Multivariate analysis[b] | | |
|---|---|---|---|---|---|---|
| | Patients | 5-year OS/ | | | | |
| Variable | n (%) | TTR (%) | P | HR | 95% CI | P |
| Total Gender | 714 (100) | | | | | |
| Female | 365 (51) | 69.0 | | 1 | | |
| Male | 349 (49) | 68.3 | 0.96 | 0.66 | 0.42-1.05 | 0.079 |
| Age[c] | | | — | 1.03 | 1.01-1.04 | 0.0066 |
| RCC2 cytosolic staining | | | | | | |
| Weak | (238) | 60.2 | | 1 | | |
| Strong | (381) | 75.2 | $8.3 \times 10^{-5}$ | 0.38 | 0.24-0.58 | $1.4 \times 10^{-5}$ |
| Stage | | | | | | |
| I | 133 (19) | 87.6 | | 1 | | |
| II | 340 (48) | 71.3 | | 2.08 | 2.17-3.70 | |
| III | 221 (31) | 55.6 | | 3.98 | 2.25-7.05 | |
| IV | 15 (2) | 28.6 | $6.2 \times 10^{-14}$ | 7.30 | 3.05-17.5 | $5.4 \times 10^{-8}$ |
| ND* | 5 (1) | | | | | |
| Tumor location | | | | | | |
| Proximal colon | 284 (40) | 68.9 | | 1 | | |
| Distal colon | 226 (32) | 67.8 | | 1.00 | 0.67-1.49 | |
| Rectum | 204 (29) | 69.2 | 0.82 | 1.14 | 0.75-1.75 | 0.78 |
| Histopathologic grade | | | | | | |
| G1 | 79 (11) | 76.6 | | 1 | | |
| G2 | 537 (75) | 69.2 | | 0.94 | 0.54-1.62 | |
| G3 | 70 (10) | 52.9 | 0.0016 | 2.06 | 1.05-4.07 | 0.0056 |

TABLE 2-continued

Univariate and multivariate analyses of correlation of cytosolic RCC2 in situ protein expression with time-to-occurrence in a consecutive CRC series.

|  | Patients | Univariate analysis[a] | | Multivariate analysis[b] | | |
|---|---|---|---|---|---|---|
| Variable | n (%) | 5-year OS/ TTR (%) | P | HR | 95% CI | P |
| Mucinous* | 9 (1) | | | | | |
| ND* | 19 (3) | | | | | |
| MSI/MSS | | | | | | |
| MSI | 103 (14) | 73.0 | | 1 | | |
| MSS | 543 (76) | 66.4 | 0.20 | 1.82 | 1.05-3.18 | 0.034 |
| ND | 68 (10) | | | | | |
| Interaction parameter | | | | | | |
| Gender x RCC2 | | | | 2.58 | 1.36-4.90 | 0.0037 |

[a]Kaplan-Meier estimate (logrank test).
[b]Cox regression model (Wald test) - all included parameters are displayed in the table.
[c]Hazard ratios are given per year of age.
*Excluded from the statistical analyses.
Abbreviations:
G1 - High differentiation;
G2 - Moderate differentiation;
G3 - Poor differentiation;
R0 - Complete resection - no residual tumor;
R1 - microscopic residual cancer at the resection margin;
R2 - Macroscopic or radiological evidence of residual cancer, locally or distant.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

The invention claimed is:

1. A method for treating colorectal cancer in a female subject diagnosed with colorectal cancer comprising:
   a) contacting a microsatellite stable (MSS) biological sample selected from the group consisting of a tumor tissue sample or a tumor biopsy sample from a female subject diagnosed with colorectal cancer with an antigen binding protein specific for regulator of chromosome condensation 2 (RCC2) polypeptide;
   b) detecting the level of said RCC2 polypeptide in said sample by detecting binding of said antigen binding protein to said RCC2 polypeptide in said sample with an immunoassay;
   c) determining that said female subject has a decreased level of said RCC2 polypeptide relative to an average RCC2 expression level in female colorectal cancer patients; and
   d) administering adjuvant chemotherapy to said female subject determined to have said decreased level of RCC2 polypeptide.

2. The method of claim 1, wherein said antigen binding protein is an antibody that specifically binds to RCC2.

3. The method of claim 2, wherein said antibody is labelled.

4. The method of claim 2, further comprising detecting said antibody that specifically binds RCC2 polypeptide with a labelled second antibody.

5. The method of claim 1, wherein said colorectal cancer is stage I, II, III or IV.

6. The method of claim 1, wherein said antigen binding protein is labelled.

7. The method of claim 1, wherein said detecting the binding of said antigen binding protein to said RCC2 polypeptide in said sample with an immunoassay comprises detecting said antigen binding protein with a labelled second antibody.

* * * * *